(12) United States Patent
Champagne et al.

(10) Patent No.: US 9,757,115 B2
(45) Date of Patent: Sep. 12, 2017

(54) EXTERNAL RETENTION MECHANISM FOR SUTURE ANCHOR

(71) Applicant: Cook Medical Technologies LLC, Bloomington, IN (US)

(72) Inventors: Elizabeth A. Champagne, Bloomington, IN (US); Ryan Nowicki, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 290 days.

(21) Appl. No.: 14/623,287

(22) Filed: Feb. 16, 2015

(65) Prior Publication Data
US 2015/0157315 A1   Jun. 11, 2015

Related U.S. Application Data

(62) Division of application No. 12/909,371, filed on Oct. 21, 2010, now Pat. No. 8,956,391.

(60) Provisional application No. 61/255,897, filed on Oct. 29, 2009.

(51) Int. Cl.
*A61B 17/04* (2006.01)
*A61B 17/02* (2006.01)

(52) U.S. Cl.
CPC ...... *A61B 17/0401* (2013.01); *A61B 17/0487* (2013.01); *A61B 17/0218* (2013.01); *A61B 2017/042* (2013.01); *A61B 2017/045* (2013.01); *A61B 2017/0414* (2013.01); *A61B 2017/0417* (2013.01); *A61B 2017/0424* (2013.01); *A61B 2017/0445* (2013.01); *A61B 2017/0446* (2013.01); *A61B 2017/0448* (2013.01); *A61B 2017/0458* (2013.01); *A61B 2017/0461* (2013.01); *A61B 2017/0496* (2013.01)

(58) Field of Classification Search
CPC ........ A61B 17/0401; A61B 2017/0414; A61B 2017/0417; A61B 2017/042; A61B 2017/0424; A61B 2017/0445; A61B 2017/0446; A61B 2017/0448; A61B 2017/045; A61B 2017/0458; A61B 2017/0461; A61B 17/0487
See application file for complete search history.

(56) References Cited

U.S. PATENT DOCUMENTS

| | | |
|---|---|---|
| 3,014,483 A | 12/1961 | McCarthy |
| 4,705,040 A | 11/1987 | Mueller et al. |
| 4,750,492 A | 6/1988 | Jacobs |
| 5,258,015 A | 11/1993 | Li et al. |
| 5,306,280 A | 4/1994 | Bregen et al. |
| 5,383,905 A | 1/1995 | Golds et al. |
| 5,536,273 A | 7/1996 | Lehrer |

(Continued)

*Primary Examiner* — Robert Lynch
(74) *Attorney, Agent, or Firm* — Woodard, Emhardt, Moriarty, McNett & Henry

(57) ABSTRACT

Among other things, embodiments of a retaining mechanism for holding a portion of the suture of a suture anchor are disclosed. When a suture anchor is inserted into a patient, the portion of the suture extending from the body is held in tension by a two-piece snap-fit mechanism. One piece has a base with an extending shaft portion and a bulbous head, and a lumen runs through the shaft. The second piece has a hole or space for snapping the second piece onto the first piece. The extending portion of the suture runs through the lumen in the first piece and can be wrapped around the shaft. Snapping the second piece onto the first contains the suture and prevents loss of tension in it.

19 Claims, 9 Drawing Sheets

(56) References Cited

U.S. PATENT DOCUMENTS

| | | | |
|---|---|---|---|
| 5,643,293 | A | 7/1997 | Kogasaka et al. |
| 5,702,397 | A | 12/1997 | Goble et al. |
| 6,010,525 | A | 1/2000 | Bonutti et al. |
| 6,086,608 | A | 7/2000 | Ek et al. |
| 6,110,183 | A | 8/2000 | Cope |
| 6,126,677 | A | 10/2000 | Ganaja et al. |
| 6,159,234 | A | 12/2000 | Bonutti et al. |
| 6,200,329 | B1 | 3/2001 | Fung et al. |
| 6,315,789 | B1 | 11/2001 | Cragg |
| 6,475,230 | B1 | 11/2002 | Bonutti et al. |
| 6,699,263 | B2 | 3/2004 | Cope |
| 7,033,379 | B2 | 4/2006 | Peterson |
| 7,033,380 | B2 | 4/2006 | Schwartz et al. |
| 7,048,755 | B2 | 5/2006 | Bonutti et al. |
| 7,090,690 | B2 | 8/2006 | Foerster et al. |
| 7,416,556 | B2 | 8/2008 | Jackson |
| 2003/0009196 | A1 | 1/2003 | Peterson |
| 2003/0167062 | A1 | 9/2003 | Gambale et al. |
| 2009/0069847 | A1 | 3/2009 | Hashiba et al. |
| 2009/0306711 | A1 | 12/2009 | Stone et al. |
| 2010/0063542 | A1 | 3/2010 | van der Burg et al. |

EXTERNAL RETENTION MECHANISM FOR SUTURE ANCHOR

REFERENCE TO RELATED APPLICATIONS

The present application is a divisional of Ser. No. 12/909,371, filed Oct. 21, 2010, now U.S. Pat. No. 8,956,391, which claims the benefit of U.S. Provisional Patent Application Ser. No. 61/255,897 filed Oct. 29, 2009 which is hereby incorporated by reference in its entirety.

The present disclosure concerns devices and methods for holding a suture under tension. In certain aspects, devices and methods are disclosed for holding under tension a suture portion of a suture anchor placed in a patient.

BACKGROUND

In many types of surgical procedures, it is known to use a suture anchor to hold tissues together. For example, in the field of gastroenterology, suture anchors have been used in enterostomy procedures to hold a portion of a viscus (e.g. the stomach or other abdominal organ) in place against another tissue portion, such as the abdominal wall or another organ. In the case of a gastrostomy, for example, a suture has a sturdy elongated piece (e.g. a thin bar or similar anchor member) that is freely movable attached at or near one end of the suture. A needle is inserted through the abdominal wall and stomach wall, and the elongated piece with the trailing suture is inserted through the needle and into the stomach. The elongated piece is longer than the width of the needle and the hole through the tissue, and so it is unable to be pulled back through the needle or hole unless it is exactly positioned along the hole or needle.

The suture extending through the tissues (and perhaps within the needle) is pulled. The pulling force is transmitted to the elongated piece, which is forced against the interior of the stomach, and pulls a portion of the stomach toward the abdominal wall. Procedures and existing suture anchors are exemplified in U.S. Pat. No. 6,699,263 to Cope, owned by the assignee of the present application and incorporated herein by reference in its entirety. The stomach tissue is pulled against the abdominal wall for ease of insertion of other devices, such as catheters for drainage or administration of therapy. The drawing together creates a seal between the abdominal wall and stomach tissues so as to help prevent fluid traffic between the stomach and abdominal cavity, which may result in peritonitis or other infections or complications involving the stomach or abdominal tissues. In some cases, the suture anchor remains in place for a period of days or weeks so as to ensure a desired engagement and stability between tissues.

One method known to keep the tension on the suture so as to maintain the tissues against each other—the stomach against the abdominal wall in the above example—uses a hemostat or other clamping device to crimp one or more metal crimp beads to the suture outside the patient. Having pulled the stomach toward and against the abdominal wall, the stomach tends to pull back on the elongated piece and suture. The crimped bead(s) hold the suture, ideally preventing it slipping through the hole in the tissue, and in the process the bead(s) are pulled against the patient's skin. While effective, this procedure has certain drawbacks. Patient discomfort and the close work of crimping the bead(s) are among such drawbacks. The size of and potential for pinching or sharp edges can injure or irritate surrounding tissue or enlarge the hole. The pull on the suture forces the bead(s) against the skin, resulting in poking discomfort from a small-surface-area item being pressed against the skin. There is a risk of slippage of the suture within the bead(s), especially if the crimp is initially insufficient. There is also the risk of cutting the suture inadvertently during crimping. Metals used for the bead(s) are generally incompatible with MRI procedures for reviewing the status of the procedure. The small size of the bead(s) and the necessity of accurate placement to ensure maintaining tension without injuring the patient makes for difficult and close work for the surgeon.

Another standard method for maintaining the tissues together is to anchor the free end of the suture in the patient's skin, as by sewing the suture into the skin directly. With at least local anesthetic from the insertion of the suture anchor, additional piercings of the skin to hold the free end of the suture may cause minimal initial discomfort, but discomfort will increase as the duration of the suture anchor in the body extends. With additional skin piercings to fasten the tensioned suture, there is also an increase in the potential for infection or other complications, and thus additional discomfort for the patient and work for the health-care provider, Accordingly, there remain needs for a suture anchor holding mechanisms that have less risk for discomfort to the patient, especially in cases where the suture anchor needs to remain in the patient for a substantial period of time, and which is easier are use than current techniques.

SUMMARY

Among other things, there is disclosed an apparatus for securing the portion of a suture anchor extending from a patient, which can include a first piece having a base with a lower surface for abutting the exterior of the skin of the patient. The first piece includes a shaft with a wrapping area adapted to accommodate a wrapped suture portion, the shaft being connected to a bulbous head. The head has a diameter larger than an outer diameter of the wrapping area of the shaft portion. The first piece also has a lumen extending through the shaft and the lower surface of the base. A second piece has an opening (e.g. a through-hole or cavity). In particular embodiments, the opening has a first portion with a first diameter approximately the same as the wrapping area or other outer diameter of the shaft portion, and a second upper portion having a configuration flaring outward to a larger diameter to accommodate the head. The lumen in the first piece is sized to permit a suture to be placed through and be slidable within it, and the second piece is configured for snap fit onto the shaft of the first piece so that the second piece is maintained on the first piece and around (e.g. against or pressing) the wrapping area of the shaft. In specific embodiments, the first piece includes a slot open to the top of the head and communicating with the lumen for accommodating a portion of the suture anchor. The head of the first piece can have a generally planar top surface that is perpendicular to the longitudinal axis of the shaft. Such a planar top surface may be positioned so that, when the first and second pieces are snapped together, the upper surface of the second piece is at least substantially coplanar or flush with the planar surface of the head. The bulbous head is spherical at least in part in some embodiments, and the upper portion of the opening of the second piece can be spherical at least in part with substantially the same radius as the spherical part or aspect of the bulbous head.

In other embodiments, the first piece has a lower surface for contacting the skin of the patient that has a rounded convex configuration. The base of the first piece may have an upper surface joining the shaft and having a rounded concave configuration, with the second piece having a lower surface with a rounded convex configuration that mates with that concave configuration. In particular embodiments, the lumen is linear throughout, having a first opening in the base and a second opening in the head, while in others the lumen has an inverted L-shape, with a first portion substantially perpendicular to the base and a second portion substantially perpendicular to that first portion and exiting the first piece at a narrowed part of the shaft portion.

A suture portion of the suture anchor is or may be wrapped around the shaft of the first piece. When the second piece snaps onto the first piece, at least part of the suture portion is captured and held between the first piece and the second piece. For example, the suture portion may be between a wrapping area of the shaft portion and a wall defining the opening in the second piece, between the head portion and the wall defining the opening in the second piece, between a bottom surface of the second piece and a facing upper surface of the first piece that are adjacent each other, or other adjacent surfaces.

In other embodiments, an external retention mechanism for a gastrointestinal suture anchor is provided, including a first unitary piece having a base in the form of a disc from which extends a shaft substantially perpendicular to the disc. The shaft has a first substantially cylindrical portion engaging the disc and a bulbous second portion opposite the disc, with the bulbous portion having a diameter greater than the diameter of the first cylindrical portion. The first piece has a lumen extending through the cylindrical and bulbous portions and between a first opening in the bulbous portion and a second opening in the disc, and a slot in the bulbous portion communicates with the lumen and is offset from the longitudinal axis of the lumen. A second unitary piece having an upper and lower surface and a hole extending between them is provided. The hole has a first substantially cylindrical portion and a second flared portion, with the first portion having a diameter approximately the same as the diameter of the first portion of the shaft, and the second portion configured to closely fit with the bulbous portion of the shaft. A suture having a distal end for insertion into a patient is threaded through the lumen.

In specific embodiments, the suture is wrapped around the substantially cylindrical portion of the shaft, e.g. so that the suture overlaps itself. A portion of the suture may be within the slot to control the suture while it is wrapped around the shaft. When assembled, a portion of the suture is preferably between the first piece and the second piece. For instance, where the second piece has a wall defining the cylindrical portion of its hole, the suture portion may be between the cylindrical surface of the shaft of the first piece and the wall of the second piece. Where the first piece has an upper surface facing the lower surface of the second piece, the suture portion may be between the upper surface of the first piece and the lower surface of the second piece.

Methods for making and using a suture retaining mechanism are also disclosed. For example, such methods might include providing apparatus as noted above, inserting a suture anchor into a patient so that a portion of the suture extends from the patient's body, wrapping the portion of the suture around the shaft of the first piece, and snapping the second piece onto the first piece so that at least part of the portion of the suture is between the first piece and the second piece. In particular embodiments, the suture portion arranged so that it extends through the lumen of the first piece and out of the head, and is wrapped sufficiently so that the portion of the suture overlaps itself. Using the suture retaining mechanism allows physicians to secure the suture without the drawbacks of bead(s) or sewing into the skin.

The physician pushes the first piece against the patient's skin to the desired tension on the suture, wraps the suture around the shaft and/or bulbous head, and snaps down the second piece onto the first piece. The mechanism can be undone by pulling off the second piece, which should require at least strong fingers or a device to be pried off, and the tension in the suture adjusted without placing a new anchor.

A gastrointestinal suture anchor system may include a first unitary piece having a base in the form of a disc from which extends a shaft portion substantially perpendicular to the base, with the shaft portion having an external wrapping area and a bulbous head portion opposite the base. The bulbous portion may have a diameter greater than that of the wrapping area, and the first piece can include a lumen extending through the wrapping area and between a first opening in the base and a second opening. A second unitary piece or cap having an upper and lower surface and an internal opening is provided. The opening has a first narrowed and/or substantially cylindrical portion and a second flared portion. The first portion of the opening may have a diameter approximately the same as the diameter of the wrapping area, and the second portion may be configured to closely fit with the bulbous head portion. A suture having a distal end for insertion into a patient is provided, with the suture being threaded through the lumen. At least one of the bulbous head portion and the second unitary piece can include a slot for guiding the suture.

In various embodiments, a suture anchor system can include a suture fixed to an anchor piece that is for insertion or is inserted into a patient, and an external retention mechanism connected to the suture. The retention mechanism includes a first piece and a second piece, each of which may be respectively unitary. The first piece has a base substantially in the form of a disc from which extends a shaft portion and a convex head portion, with the shaft portion defining an external wrapping area for the suture, and a lumen extends from a first opening in the base to a second opening. The second or cap piece has a lower edge and an opening at least partly circumscribed by the lower edge, and is configured to snap-fit over the first piece's head portion. When the second piece is snapped onto the first piece, a portion of the second piece is in close proximity or engagement with the wrapping area. The retention mechanism provides a path from the wrapping area out of the retention mechanism substantially along the base and/or between the second piece and the base of the first piece. The shaft portion can be substantially perpendicular to the base and terminates in the head portion. The suture may have a distal end fixed to the anchor piece, a free proximal end and a length in between those ends, with a portion of that length entering the lumen through said first opening and exiting said lumen through said second opening. In particular embodiments, only one part of the suture extends through the retention mechanism, i.e., the suture does not double back through the retention mechanism.

DETAILED DESCRIPTION OF THE ILLUSTRATED EMBODIMENTS

Figure 1:
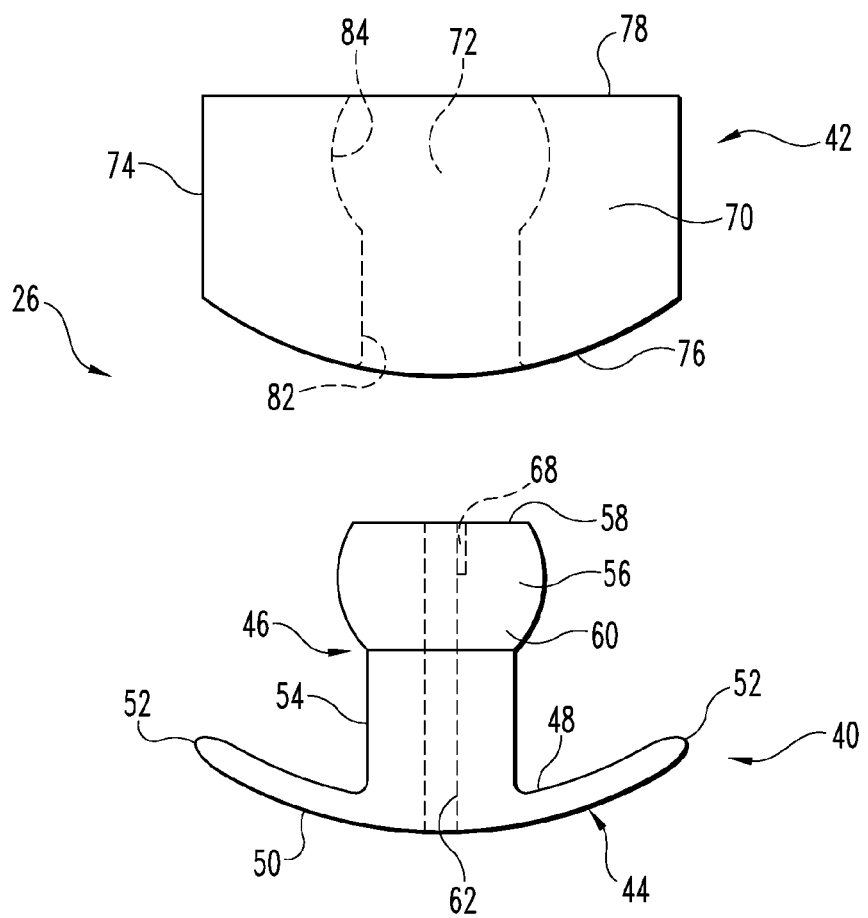
FIG. 1 is an exploded view of an embodiment of a mechanism for holding a suture in tension according to the present disclosure.
Figure 2:
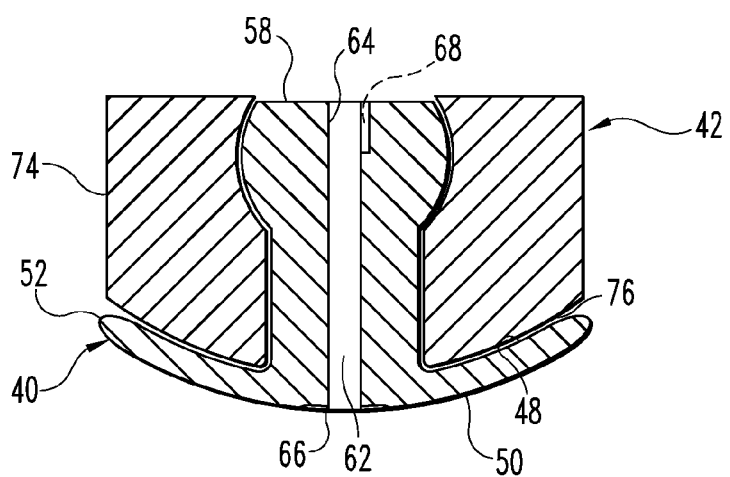
FIG. 2 is a cross-sectional view of the embodiment of FIG. 1 in assembled condition.
Figure 3:
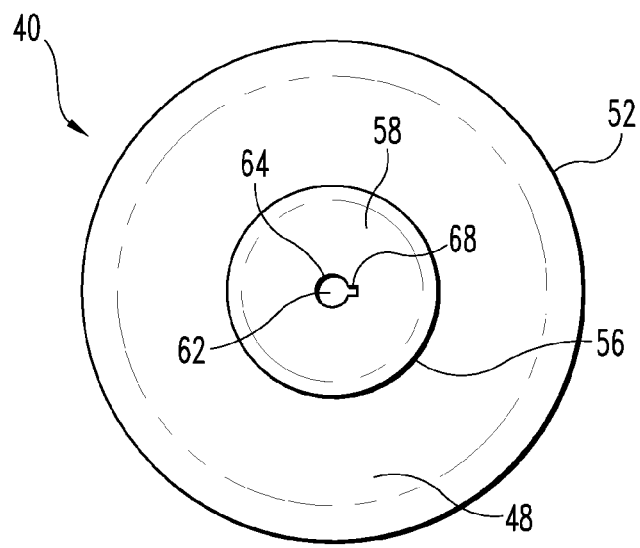
FIG. 3 is a top view of one part of the embodiment of FIG. 1.
Figure 4:
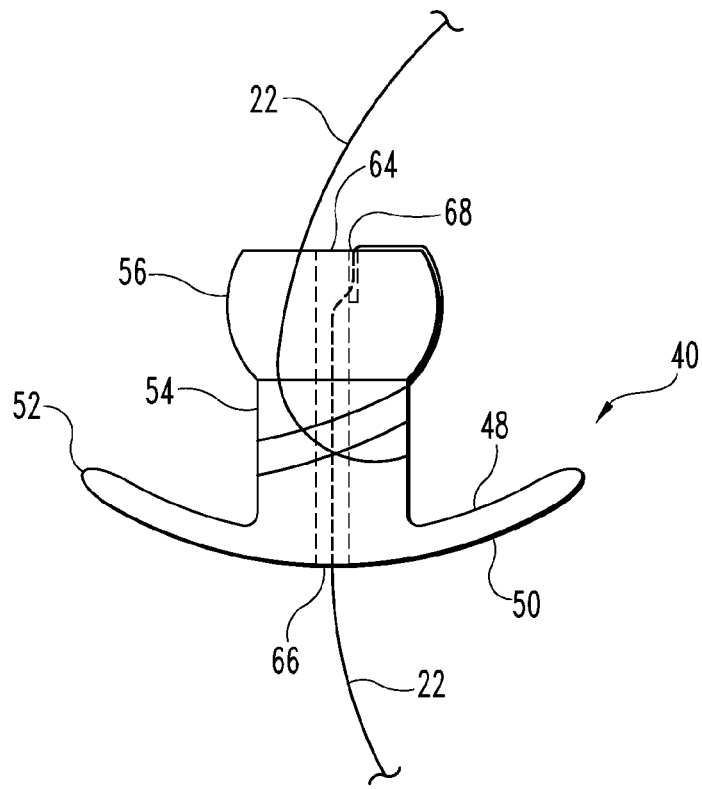
FIG. 4 is a side view of the part shown in FIG. 3 connected to a suture.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

Referring generally to the drawings, an embodiment of a suture anchor 20 includes a suture 22 and an elongated anchor member 24 at one end of suture 22. An embodiment of a holding mechanism 26 for anchoring the free proximal portion of suture 22 is disclosed. As will be indicated further below, anchor 20 is inserted into the body to hold tissues together, with mechanism 26 providing secure and comfortable holding of suture 22.

Suture 22 is an elongated filament adapted to be threaded through a narrow opening in a needle into a viscus (e.g. the stomach) of a patient. Suture 22 is strong enough in a particular embodiment pull the viscus toward and against other body tissue without snapping, and is constructed according to known techniques. Suture 22 has a first distal end 30 which is fixed to anchor member 24 and a free proximal portion 32 that extends away from anchor member 24.

Figure 5:
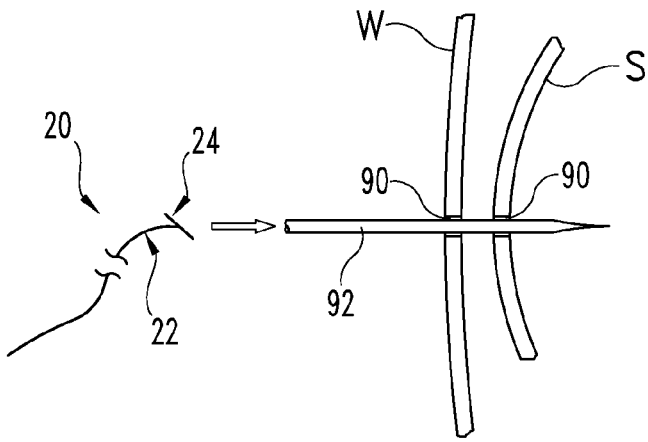
FIGS. 5-7 is a schematic view of insertion of a suture anchor into the stomach through the abdominal wall of a patient.
Figure 6:
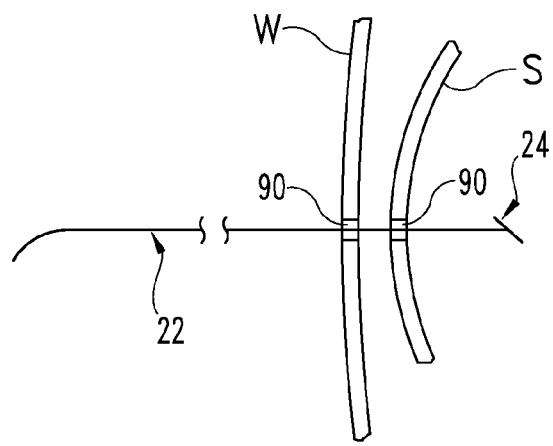

Anchor member 24 is an elongated member in the illustrated embodiment. As indicated, distal end 30 of suture 22 is fixed to anchor member 24, and in the illustrated embodiment (FIG. 5), the point of fixation is approximately the center of anchor 24. Anchor member 24 may be a spring device as shown and described in U.S. Pat. No. 6,699,263 to Cope, incorporated herein by reference in its entirety. In other embodiments, anchor member 24 may be a bar, rod or other elongated solid structure. Anchor member 24 is sized in cross-sectional width or diameter relatively small so as to be insertable through a needle into a viscus, yet of a width or diameter so as not to be bent to a degree that would allow it to enlarge the hole through the tissue and/or be pulled back through the hole. Suture 22 may be fixed to anchor member 24 by tying, gluing, wrapping or a variety of other ways.

Mechanism 26 includes a first piece 40 and a second piece 42 configured to fit together in a unit. First piece 40 is monolithic in this embodiment, and includes a base 44 and a shaft 46 extending from base 44. Base 44 is a circular disc in the illustrated embodiment, having a first surface 48 from which shaft 46 extends, a second opposite surface 50, and a perimeter edge 52. It will be seen that base 44 may be formed in other shapes, but shapes without sharp corners (e.g. circles or ovals) are less likely to provide discomfort to the patient during use.

Surface 48 is concave in the illustrated embodiment, and may be thought of as an "upper" surface insofar as it points away from the patient during use, as will be further explained below. Surface 50 (which may be thought of as a "lower" surface insofar as it abuts the skin during use) is convex in the illustrated embodiment, and may have a curvature substantially the same as or complementary to the curvature of surface 48. The similar or identical curvatures of surfaces 48 and 50 provide more surface area between them (compared to facing flat surfaces) without substantial additional bulk, resulting in greater friction and stability between the surfaces and better holding of suture 22 if it is between them, as discussed below. Nonetheless, surfaces 48 and 50 may each be flat, or may have differing curvatures or configurations, in other embodiments. Edge 52 is rounded where it meets surfaces 48 and 50, and in a particular embodiment edge 52 has a continuous uniform curve between surfaces 48 and 50. In embodiments in which surface 50 has a steeper or sharper curvature than that of surface 48, edge 52 between them may have very little thickness, essentially forming a rounded circular line between surfaces 48 and 50.

The illustrated embodiment of shaft 46 is centered in base 44 and extends substantially perpendicularly to the portion of base 44 to which it is connected. Where the curvature of surface 48 is spherical or part-spherical, as in this embodiment for example, shaft 46 extends along a radius of that sphere. Shaft 46 includes a substantially cylindrical portion 54 adjoining base 44 and a bulbous head 56. Cylindrical portion 54 has a diameter smaller than the width or diameter of base 44, and forms a wrapping area for suture 22, as will be noted further below. A particular area for wrapping suture 22 may be the area of shaft 46 immediately below head portion 56, since if suture 22 is wrapped so that a portion contacts head portion 56, the configuration of head portion 56 combined with the tension on suture 22 when wrapping tends to move the suture to the upper portion of shaft 46. Head 56 has a width or diameter greater than that of cylindrical portion 54, and in the illustrated embodiment is spherical in part with a flattened surface 58 opposite cylindrical portion 54. A lower portion 60 of head 56 is generally opposite surface 58 and generally facing surface 48 of base 44. In other embodiments, head 56 has a toroidal or donut-shaped lateral surface around surface 58, or lower portion 60 is configured as a flat ledge.

First piece 40 further includes a lumen 62 that extends through shaft 46 and base 44. A first opening 64 of lumen 62 is in shaft 46 (e.g. in flattened surface 58 of head 56), and a second opening 66 of lumen 62 is in base 44 (e.g. in convex surface 50). Lumen 62 is linear, i.e. along a straight line, throughout its length in the illustrated embodiment, having a central longitudinal axis. A slot 68 is placed on one side of lumen 62, and in this particular embodiment slot 68 is radial with respect to lumen 62, i.e., slot 68 points toward the central longitudinal axis of lumen 62. Slot 68 is open at the top of head 56 in this embodiment, so that a portion of slot 68 adjoins opening 64 of lumen 62.

Second piece 42 of mechanism 26 is monolithic in the illustrated embodiment, and is configured as a perforated disc or washer, having a body 70 through which a hole 72 extends. Body 70 has an exterior shape that is generally complementary to the surface 48 and edge 52 of piece 40. In the illustrated embodiment, where base 44 of piece 40 is circular and has a concave surface 48, body 70 is configured to have a circular edge 74 and have approximately the same diameter as base 44, so that edge 74 generally lies atop edge 52 when pieces 40 and 42 are assembled. A convex surface 76 configured to closely fit or mate with surface 48. Body 70 has a surface 78 facing opposite to surface 76 and toward head 56 when assembled, and in the illustrated embodiment surface 78 is flat or planar.

Hole 72 extends between surfaces 76 and 78 and is open at both surfaces. Hole 72 has a first portion 82 adjoining surface 76 that is substantially cylindrical, having a diameter substantially the same as or slightly larger than that of cylindrical portion 54 of shaft 46. A second portion 84 of hole 72 adjoins surface 78 and is complementary to bulbous head 56 of shaft 46. For example, in the embodiment in which lower portion 60 of head 56 is spherical, portion 84 of hole 72 is also spherical. Portion 84 has a greater width or diameter than that of portion 82 and cylindrical portion 54 of shaft 46, and in the illustrated embodiment has a close fit with at least portion 60 of head 56. The length of hole 72 (and of its parts 82 and 84) in this particular embodiment is the same as the length of shaft 46 (and of its parts 54 and 56), so that the flattened surface 58 of shaft 46 is at least approximately flush with surface 78 of piece 42, and the respective cylindrical and bulbous or spherical portions of hole 72 and shaft 46 fit closely together.

The length of the cylindrical first portion 82 of hole 78 is approximately the same as the length of cylindrical portion 54 of shaft 46. In a particular embodiment, the length of portion 82 is at least slightly smaller than that of portion 54 of shaft 46. In that case, when piece 42 is snapped onto piece 40, portion 60 of head 56 engages the wall around portion 82 of hole 78. This provides a force pressing surface 76 of body 70 against surface 48 of piece 40, and portion 60 of head 56 against an edge or surface of the wall around portion 82 of hole 78.

Pieces 40 and 42 are assembled together by inserting shaft 46 into hole 72. Head 56 of shaft 46 is forced through the cylindrical portion 82 of hole 72 and into portion 84 of hole 72. Pieces 40 and 42 thus snap together, and are held together with most or all of head 56 within portion 84 of hole 72 and cylindrical shaft portion 54 within cylindrical hole portion 82. Piece 42 is retained on piece 40 by virtue of interference between the larger-diameter head 56 and the smaller-diameter cylindrical hole portion 82. Lower portion 60 on head 56 is adjacent to or engages a shoulder formed where hole portions 82 and 84 meet, preventing unintentional removal of piece 42 from piece 40.

As will be discussed further below, mechanism 26 is connected to suture 22 so that suture 22 is locked with respect to mechanism 26. Free or proximal end 32 of suture 22 is threaded through lumen 62 of piece 40, and in the illustrated embodiment end 32 extends from opening 64 of lumen 62. In certain embodiments, mechanism 26 is provided with at least piece 40 pre-loaded on the free end 32 of suture 22, with surface 50 of piece 40 generally facing anchor 24 and surface 48 of piece 40 generally facing free end 32 of suture 22. As another example, pieces 40 and 42 may be initially snapped together as indicated above, and suture 22 may be threaded through lumen 62 as indicated, with a loop, knot, collar or similar item in or on suture 22 to prevent mechanism 26 from falling off suture 22. When using such an example of mechanism 26, as further described below, piece 42 is pulled off of piece 40 by the surgeon, the suture is manipulated, and piece 42 is replaced. In other embodiments, mechanism 26 may be connected to suture 22 following insertion of suture anchor 20 into the body.

For simplicity, an example of the use of mechanism 26 with suture anchor 20 will now be described with reference to a gastrostomy procedure, i.e., a creation of an opening into the stomach through the abdominal wall. It will be understood that the structure and methods disclosed herein are useful in other types of procedures as well.

Referring generally to FIGS. 5-10A, there is shown schematically a portion of the stomach S and the abdominal wall W of a patient. A passageway 90 is established from outside the body through the skin and wall W to the interior of the stomach S by a puncture from needle 92. Needle 92 is advantageously a relatively small gauge needle, such as 18 gauge and about 7 centimeters in length. Needle 92 is advanced through the abdominal wall W and into the stomach S. Fluoroscopic or other guidance can be used to ensure proper insertion of needle 92. One or more suture anchors 20 are introduced into needle 92 so that anchor member 24 of each suture anchor 20 is forward in the needle. A wire guide or other device (not shown) is inserted through needle 92 to push anchor member(s) 24 out of the insertion end of needle 92. With anchor member(s) 24 within the stomach S, needle 92 can be withdrawn, while the guide, cannula or other device can be left in place, if desired.

The surgeon pulls on suture 22 so that anchor member 24 engages the interior surface of the stomach S. Further pulling draws the engaged part of stomach S toward the abdominal wall W. The surgeon continues pulling on suture 22 until the engaged part of stomach S is positioned as desired with respect to wall W, which in particular embodiments is in engagement with wall W. As noted above, having stomach S in engagement with wall W (or other tissue portions in engagement with each other) reduces the chance of bodily fluids, bacteria or other potential hazards entering a region of the body where they should not be.

Figure 7:
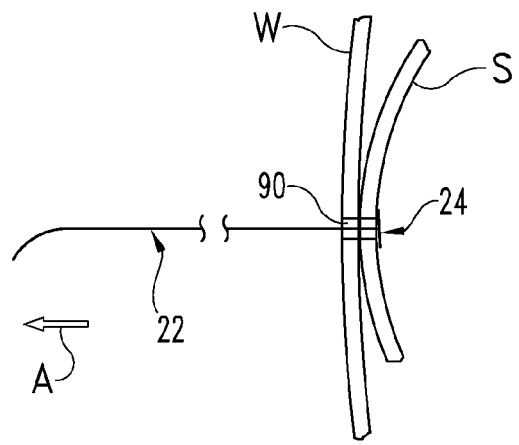
Figure 8:
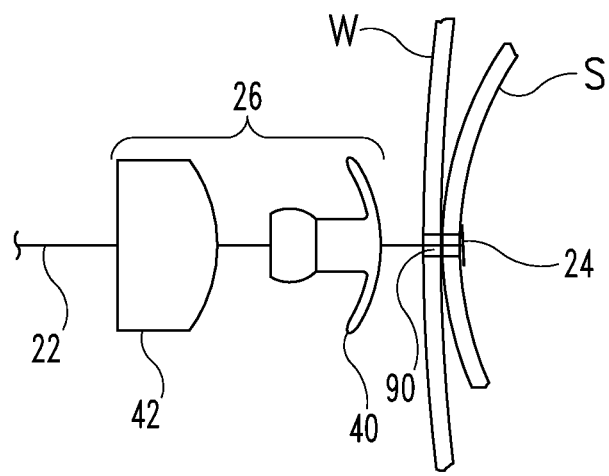
FIG. 8 is a schematic view of the placement of the embodiment shown in FIG. 1 with respect to a suture anchor placed as in FIGS. 5-7.
Figure 9:
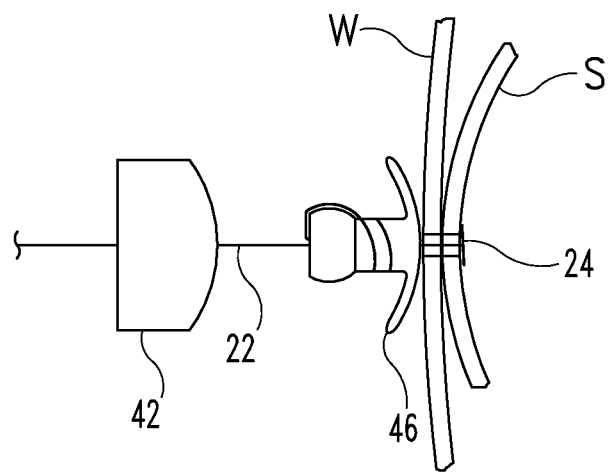
FIG. 9 is a schematic view of a part of the embodiment shown in FIG. 1 placed as in FIGS. 5-7 with a portion of the suture of a suture anchor wrapped around a portion of it.

Once anchor member 24 is deployed, proximal portion 32 of suture 22, which extends outside the patient, is grasped and suture 22 is pulled in the general proximal direction indicated by arrow A (FIG. 7). Such pulling causes anchor member 24 to engage a portion of the internal wall of stomach S perpendicular to the needle hole used for insertion, as depicted in FIG. 7. Further pulling on suture 22 in the general proximal direction moves the wall of stomach S to a position adjacent or preferably contacting abdominal wall W. With a portion of stomach S firmly retracted against abdominal wall W, the chance of intraperitoneal leakage or similar complications are reduced or eliminated. Tension on suture 22 is maintained until mechanism 26 is placed.

As noted above, mechanism 26 may be previously loaded on suture 22, or may be placed on suture 22 following insertion of suture anchor 20 into the patient, and suture 22 extends through lumen 62 and out opening 64 of piece 40. With suture 22 tensioned so that the relevant part of stomach S is positioned as the surgeon desires, and with piece 42 disconnected from piece 40, piece 40 is advanced along suture 22 so that its surface 50 contacts the skin of the patient. The tension on suture 22 is maintained as the surgeon wraps a portion of it around shaft 46 of piece 40 one or more times. In the illustrated embodiment of shaft 46, any part of shaft 46 can be a wrapping area for suture 22, although portion(s) adjacent head portion 56 may be more useful or accessible for wrapping because of the curvature of head portion 56 and any curvature that may be in base 44. In embodiments of piece 40 that include slot 68, a portion of suture 22 enters slot 68 during wrapping or is placed in slot 68 just before wrapping begins. Slot 68 provides a side surface that prevents suture 22 from circling hole 78 as the surgeon wraps it under tension. The tension on the wrapped suture 22 creates friction between suture 22 and shaft 46, which helps maintain the tension. The curved surface of head portion 56 tends to work with the tension in suture 22 to guide a portion of the suture wrapped on or contacting that curved surface toward the wrapping area of shaft 46. Wrapping suture 22 around shaft 46 twice or more, particularly where a portion of suture 22 overlaps itself, provides additional friction and gripping force to maintain the tension in suture 22.

With a portion of the middle of suture 22 wrapped around shaft 46, piece 42 is placed on piece 40 to hold and lock suture 22. In the illustrated embodiment, piece 42 is initially threaded onto suture 22 so that suture 22 extends through hole 72 of piece 42. In that case, piece 42 is moved along suture 22 and against head 56 of piece 40. Pressure on piece 42 or on both pieces 40 and 42 forces shaft 46 through hole 72, snapping pieces 40 and 42 together. The convex curvature of surface 50 which turns edge 52 up from the skin can provide a holding or pressing surface to aid snapping piece 42 on.

Suture 22, which is wrapped around shaft 46, is covered, trapped or pinched between shaft 46 and the wall of hole 72. The wrapped suture 22 does not lose tension because of the friction between it and one or both of shaft 46 and piece 42, particularly if suture 22 overlaps itself. As will be apparent from the drawings and the prior discussion, with suture 22 extending out of lumen 62, along head portion 56 and wrapped around an area of shaft 46, as piece 42 is snapped onto piece 40 any drag exerted by piece 42 on suture 22 tends to pull suture 22 through lumen 62 against anchor 24, increasing tension on suture 22 and the hold of mechanism 26 on suture 22. Suture 22 is between the cylindrical portion of shaft 46 and the cylindrical wall of piece 42 that defines hole 72, between part of head 44 and the flared wall of piece 42 that devices the upper portion of hole 72, between surfaces 48 and 50 of pieces 40 and 42, and/or between other parts of pieces 40 and 42. Piece 42 covers the part of suture 22 wrapped around or adjacent shaft 46, keeping other agents from contacting that portion of suture 22 and loosening it. In certain embodiments, the tolerances between pieces 40 and 42 are determined so that at least some of suture 22 is engaged by both pieces 40 and 42.

Figure 10:
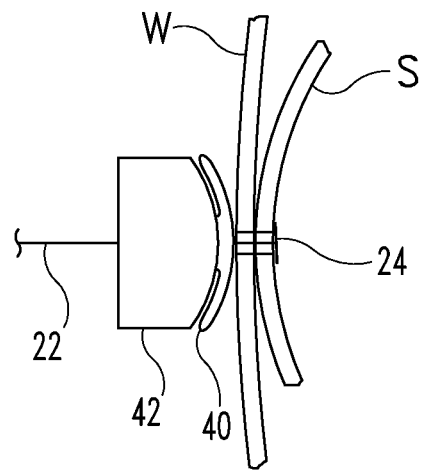
FIG. 10 is a schematic view of the embodiment shown in FIG. 1 placed as in FIG. 57 holding the suture in tension, with a portion of the suture extending from the top of the mechanism.
Figure 10A:
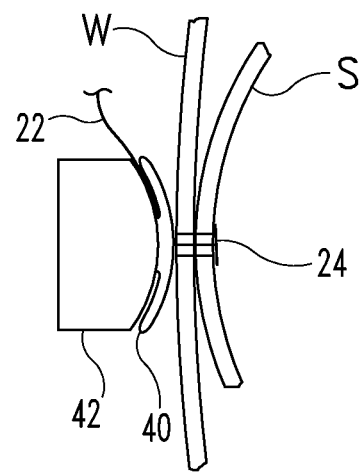
FIG. 10A is a schematic view of the embodiment shown in FIG. 1 placed as in FIGS. 5-7 holding the suture in tension, with a portion of the suture extending from the side of the mechanism.
Figure 11:
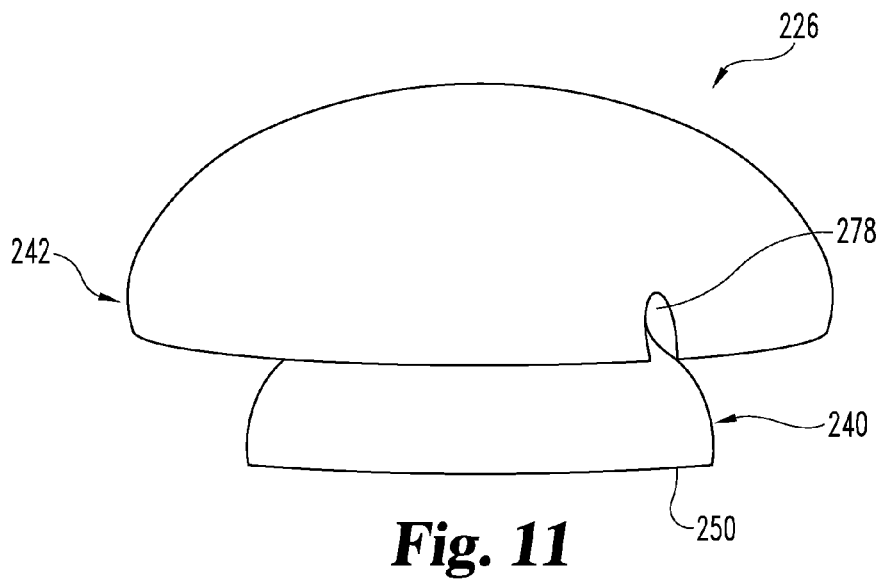
FIG. 11 is a side elevational view of an embodiment of a mechanism for holding a suture in tension according to the present disclosure.
Figure 12:
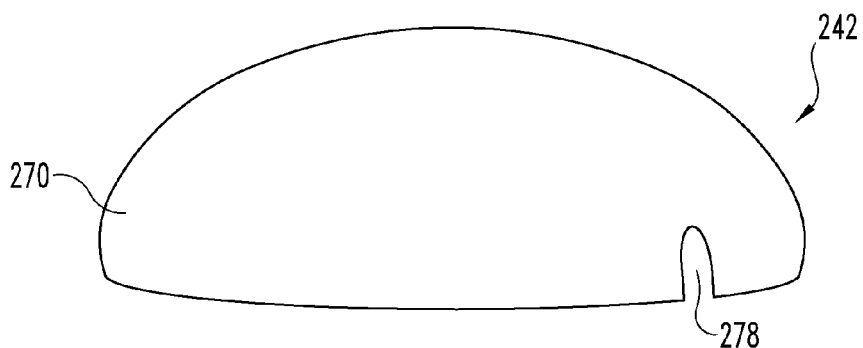
FIG. 12 is a side elevational view of an embodiment of part of the mechanism embodiment of FIG. 11.
Figure 13:
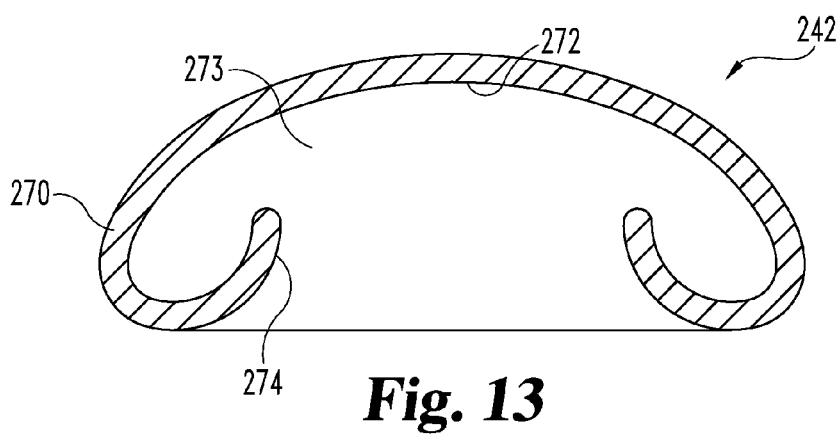
FIG. 13 is a cross-sectional view of the embodiment of FIG. 12 taken in the plane of the page of FIG. 12.
Figure 14:
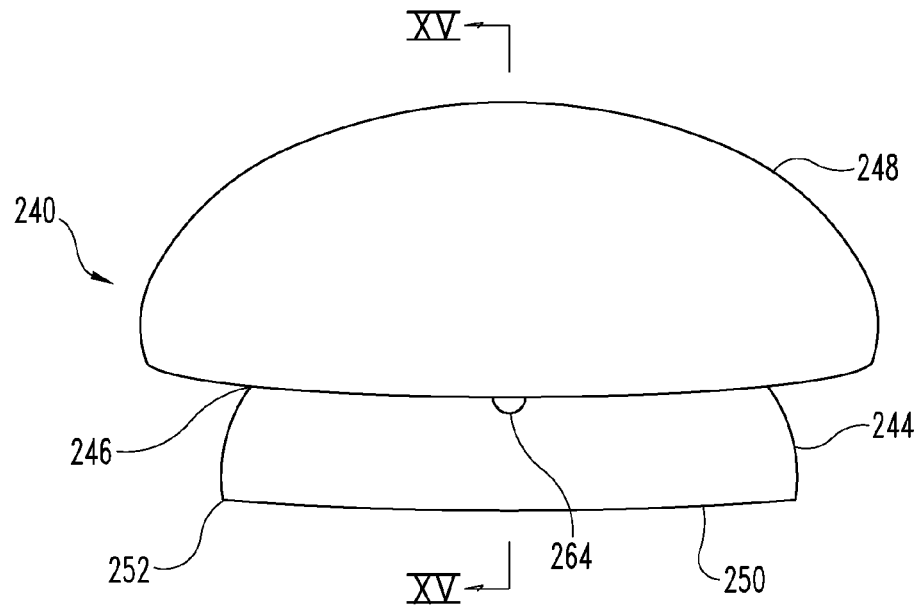
FIG. 14 is a side elevational view of an embodiment of part of the mechanism embodiment of FIG. 11.
Figure 15:
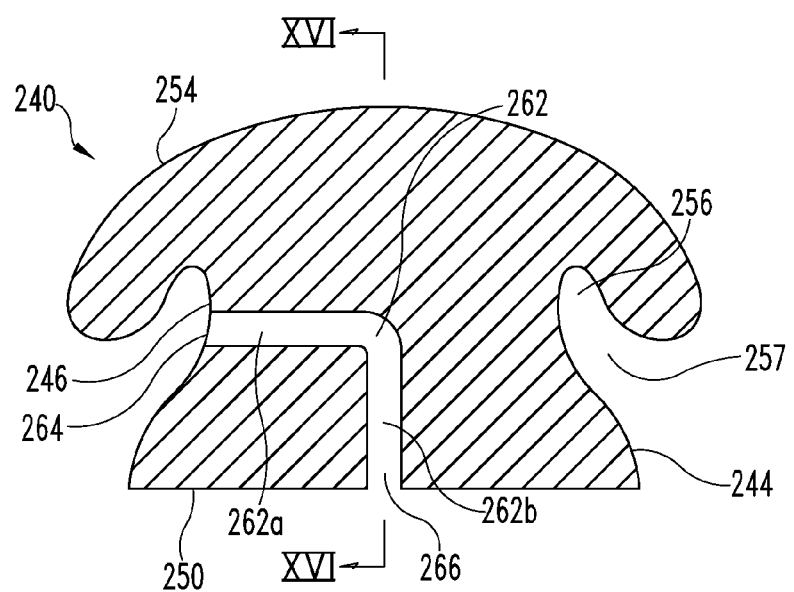
FIG. 15 is a cross-sectional view of the embodiment of FIG. 14 taken along the lines XV-XV in FIG. 14 and viewed in the direction of the arrows.
Figure 16:
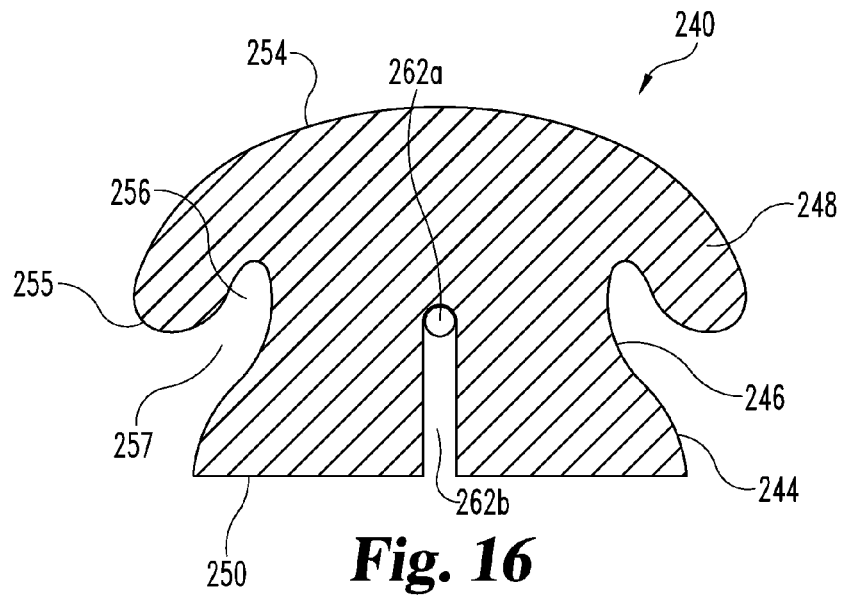
FIG. 16 is a cross-sectional view of the embodiment of FIG. 14, taken along the lines XVI-XVI of FIG. 15 and viewed in the direction of the arrows.

The portion of suture 22 extending from the hole 72 can be cut off. In embodiments in which suture 22 is not already through hole 72 of piece 42, suture 22 can be inserted through hole 72 and piece 42 snapped onto piece 40 as previously described. Alternatively, suture 22 need not extend through hole 72, and in that case snapping piece 42 on piece 40 will result in suture 22 lying between surface 76 of piece 42 and surface 48 of piece 40, as indicated in FIG. 10A. A close fit of pieces 40 and 42 provides pinching or friction on suture 22 to maintain its tension in addition to the friction or interference of any wrapping of suture 22 around shaft 46.

With mechanism 26 assembled around suture 22 as indicated, the tension on suture 22 that holds the relevant portion of stomach S in position with respect to abdominal wall W is maintained. That tension holds tissue of stomach S and abdominal wall W together and presses mechanism 26 against the skin. The convex underside 50 in the illustrated embodiment of piece 40 spreads the tension force along a significant surface area of the skin, so as to minimize or eliminate discomfort, bruising, laceration by the suture, or other damage to the patient. With circular base 44 and rounded edge 52 of the illustrated embodiment, sharp edges do not dig into the skin. The flattened surface 58 and approximately flush surface 78 of piece 42 maintain a relatively low profile next to the skin. Piece 42 is held so that it will not inadvertently pop off of piece 40, yet a physician or other medical professional can pry piece 42 off with strong fingers or a prying tool inserted between surfaces 76 and 48.

At some point the physician may wish to adjust or release the tension on suture 22, for example when the tissue of stomach S and/or wall W has become accustomed to its new location, new tissue has grown between stomach S and wall W, a therapeutic or drainage device has been adequately placed and supported, or when it is no longer needed. At that time, piece 42 is pulled off piece 40, and suture 22 is unwrapped from piece 40. If adjustment is desired, suture 22 is pulled or released and re-wrapped around shaft 46 to provide the desired greater or lesser tension on suture 22, and piece 42 is re-snapped onto piece 40. If removal is desired, suture 22 is unwound from shaft 46 (if it has not unwound by itself after piece 42 is pulled off), and piece 40 is removed from the patient's skin, with suture 22 passing through lumen 62 and out of opening 66 in surface 50 of piece 40. The portion of suture 22 extending from the skin can be cut, and the anchor 24 and portion of suture 22 between anchor member 24 and the skin surface can pass into the gastrointestinal tract and be eliminated.

Referring now generally to FIGS. 11-18, mechanism 226 includes a first piece 240 and a second piece 242 configured to fit together in a unit. First piece 240 is monolithic in this embodiment, and includes a base portion 244, a shaft or waist portion 246 extending from base portion 244, and an overhanging top or bulbous head portion 248. Base portion 244 is principally circular or cylindrical in this embodiment, with its upper extent beginning to narrow into shaft portion 246. Base portion 244 also includes a lower surface 250 that contacts the patient's skin, and a perimeter edge 252. It will be seen that base 244 may be formed in other shapes, but shapes without sharp corners (e.g. circles or ovals) are less likely to provide discomfort to the patient during use. Surface 250 (which may be thought of as a "lower" surface insofar as it abuts the skin during use) is flat or planar in the illustrated embodiment, and may have a curvature substantially the same as or similar to the convex curvature of surface 50 of piece 40 discussed above. Surface 250 may have differing curvatures or configurations in other embodiments. Edge 252 around surface 250 is rounded, and in a particular embodiment edge 252 has a continuous uniform curve from surface 250 in to the side surface of shaft 246.

In this illustrated embodiment, shaft 246 is a short portion contiguous with base 244. Base 244 and shaft 246 in this embodiment share an outer surface approximately the shape of half of an hourglass, with a generally convex or cylindrical lower exterior generally corresponding to base portion 244 that curves into a generally conical or concave exterior generally corresponding to shaft or waist portion 246. In a longitudinal cross-section, base portion 244 and shaft portion 246 have a general S-shape. Shaft 246 thus becomes thinner in diameter, while remaining substantially circular in lateral cross-section in this embodiment, adjoining both base portion 244 and overhanging head 248.

Head portion 248 has a width or diameter greater than that of shaft 246 and base 244, and in the illustrated embodiment has an upper surface 254 that is rounded or spherical in part with an overhanging edge portion 255. The overhanging edge portion 255 is shown as rounded in the present embodiment, but in other embodiments, edge portion 255 may end in a sharpened or pointed portion. Edge portion 255 defines an annular channel 256 between head portion 248 and one or both of shaft portion 246 and base portion 244. Channel 256 is annular as head portion 248 is substantially in the form of a complete circle that encloses most of channel 256, leaving only an inlet 257 allowing entrance or exit from channel 256 between head portion 248 and one or both of shaft portion 246 and base portion 244.

First piece 240 further includes a lumen 262 that extends within shaft portion 246 and base portion 244. The illustrated embodiment shows a first lumen portion 262a pointing generally parallel to surface 250, and a second lumen portion 262b extending from lumen portion 262a through shaft 246 and base 244. A first opening 264 in one or both of shaft 246 and base 244 opens lumen portion 262a to the exterior of piece 240. The illustrated embodiment shows opening 264 to be in a concave or conical portion of the exterior of piece 240 that slopes generally toward the center of piece 240 traveling toward head portion 248. A second opening 266 is in base 244 (e.g. through surface 250) that opens lumen portion 262b. While each part 262a, 262b of lumen 262 is linear in this embodiment, lumen 262 in its entirety is not linear. For example, lumen 262 may be substantially in the shape of an inverted L, with lumen portions 262a and 262b being substantially perpendicular to each other. Lumen 262 is rounded in this embodiment, for example generally cylindrical or circular-cylindrical.

It will be seen that the illustrated embodiment of piece 240 is substantially mushroom-shaped, with base portion 244 and shaft portion 246 forming a "stem" that slopes or angles in toward the center, and head portion 248 forming a "cap" that spreads or overhangs the "stem." As will be explained further below, the mushroom-like configuration has advantages over other devices.

Second piece 242 of mechanism 226 is monolithic in the illustrated embodiment, and is configured as a covering snap-on cap that covers all of head portion 248 of piece 240. Piece 242 has a body 270 with an interior surface 272 defining a space 273, and further includes a reverted edge 274. Space 273 is configured to enclosed top portion 248 of piece 240, with reverted edge 274 occupying channel 256, when pieces 240 and 242 are assembled. Thus, body 270 has an interior shape that is generally complementary to top portion 248 and its overhanging portion 255. In particular embodiments, body 270 is configured so that space 273 is configured substantially identically to top portion 248 or slightly smaller than top portion 248, to give a snug or tight fit with piece 240. For example, reverted edge 274 may fill substantially the entirety of channel 256, so that edge 274 engages or has a press-fit with the exterior of shaft portion 246 and possibly a portion of base 244. In the illustrated embodiment, where piece 240 is generally circular and has a concave, conical or otherwise indented shaft portion 246, body 270 is larger in diameter than head portion 248 (and consequently larger in outer diameter than base 244 and shaft 246), so that edge 274 generally lies over edge 255. At least part of piece 242 (e.g. edge 274) and/or at least part of piece 240 (e.g. edge 255 or all of top portion 248) may be flexible or compressible to allow easier assembly of pieces 240, 242 together. Through one side of body 270 a slot 278 is placed. In the particular illustrated embodiment slot 278 is radial with respect to piece 242, i.e., slot 278 points toward the central longitudinal axis of piece 242 (and piece 240 when pieces 240, 242 are engaged).

Use of mechanism 226 will be described in the context of the suture and anchor embodiments discussed above, and in the same medical context. As previously noted, such structure and the methods described herein may be useful in other procedures or contexts or with other structures as well.

Figure 17:
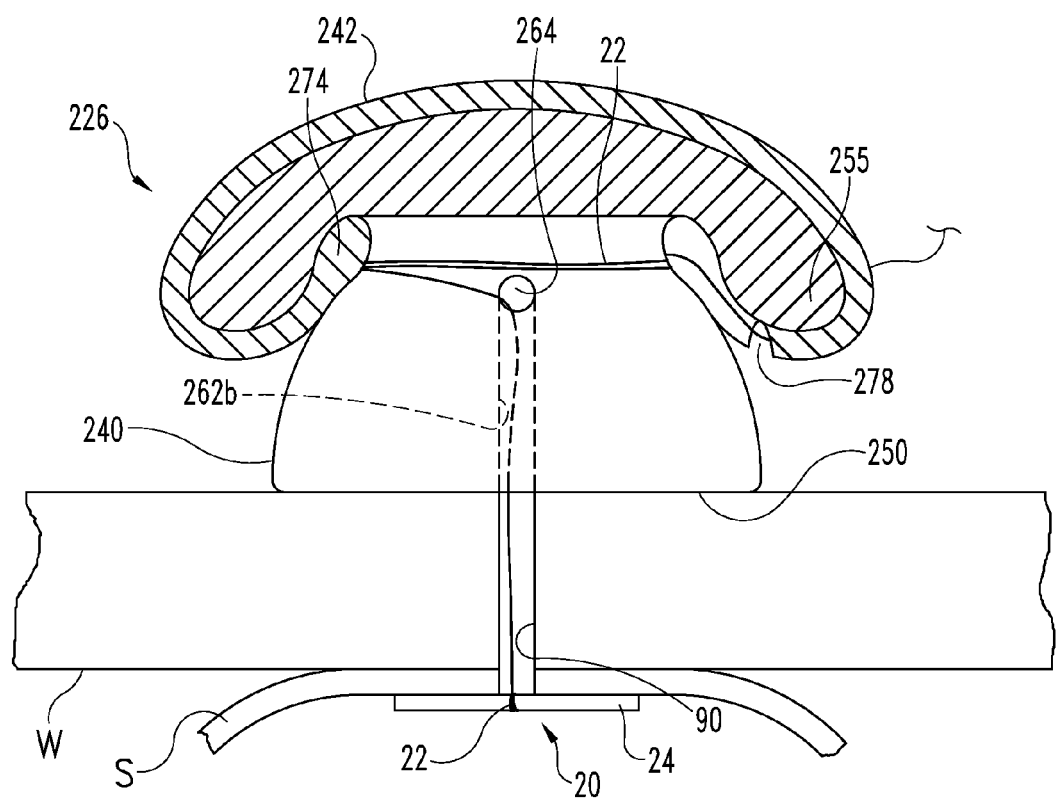
FIG. 17 is a part cross-sectional view of the embodiment of FIG. 11 in use.
Figure 18:
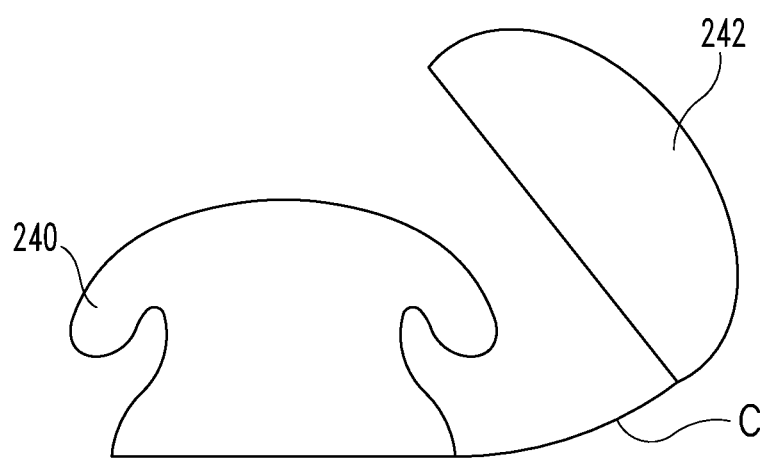
FIG. 18 is a side elevational view of an embodiment of the mechanism of FIG. 11 with a connection.

Referring generally to FIG. 17, and akin to FIGS. 5-10A, there is shown schematically a portion of the stomach S and the abdominal wall W of a patient. As is described above with respect to FIGS. 5-10A, a passageway 90 is established and one or more suture anchors 20 are introduced through passageway 90 into the patient. The surgeon pulls on suture 22 so that anchor member 24 engages the interior surface of the stomach S and stomach S is positioned as desired with respect to wall W, which as noted above may be in engagement with wall W. Tension on suture 22 is maintained until mechanism 226 is placed.

As with mechanism 26, mechanism 226 may be previously loaded on suture 22, or may be placed on suture 22 following insertion of suture anchor 20 into the patient. Suture 22 extends through lumen 262, i.e., from the patient, suture 22 enters lumen portion 262b through opening 266, extends through lumen portions 262b and 262a, and exits piece 240 via opening 264. As will be seen in the drawings, in the illustrated embodiment suture 22 does not double back on itself and is not looped within lumen 262, but moves directly in one direction through lumen 262. Suture 22, as with the example of mechanism 26 described above, does not enter the body via one part of the device and exit through another, but provides a simpler device in which suture 22 only exits the body, through lumen 262. With suture 22 tensioned so that the relevant part of stomach S is positioned as the surgeon desires, and with piece 242 disconnected from piece 240, piece 240 is advanced along suture 22 so that its surface 250 contacts the skin of the patient. As piece 240 is advanced, suture 22 threads through lumen 262 and out from under edge 255 of piece 240.

The surgeon proceeds to wrap suture 22 around piece 240 one or more times while maintaining tension on suture 22. In particular embodiments, wrapping suture 22 two to six times around piece 240 is believed to be quite effective. The wrapping or winding of suture 22 is guided by edge 255, so that suture 22 turns around the portion of piece 240 adjacent lumen portion 262a. In the illustrated embodiment, where shaft portion 246 adjacent to (and roughly the same height from surface 250 as) lumen 262a is inwardly-sloped, that slope tends to move tensioned suture 22 to the minimum-diameter portion of piece 240 as it is wrapped. Thus, the shape of this embodiment of piece 240 guides wrapping and results in wrapped suture 22 being located in a central wrapping area at least partly within or near channel 256. The tension on the wrapped suture 22 creates friction between suture 22 and shaft portion 246, and the inward slope tends to move suture loops toward the thinnest portion of shaft 246 and next to or over each other, which helps maintain the tension. Wrapping suture 22 around shaft 246 twice or more, particularly where a portion of suture 22 overlaps itself, provides additional friction and gripping force to maintain the tension in suture 22.

With a portion of the middle of suture 22 wrapped around shaft 246, piece 242 is placed on piece 240 to hold and lock suture 22. In the illustrated embodiment, in which piece 242 includes slot 278, piece 242 is oriented so that edge 274 of piece 242 is above or in contact with head portion 248 of piece 240 and suture 22 extends through slot 278 of piece 242. Pressure on piece 242 or on both pieces 240 and 242 forces head portion 248 into space 273, snapping pieces 240 and 242 together. Edge 274 of piece 242 occupies channel 256, filling channel 256 substantially completely in the illustrated embodiment. As indicated above, the convex surface of top 248 and/or the slope of edge 274 of piece 242 tend to spread edge 274 and/or compress head portion 248 or edge 255, to allow the snap-fit. It will be seen that piece 242 does not exert much if any drag against suture 22 when being snapped on. Due to the positioning of the opening of lumen 262 and the curvature of piece 240 in this embodiment, when piece 242 is snapped on it does not travel along suture 22 to a significant degree, but tends to exert force normal to the surface of shaft portion 246 as edge 274 clears top 248, or to exert force on suture 22 generally toward top 248 of piece 242 as edge 274 enters channel 256.

Suture 22, after wrapping around shaft 246, is covered, trapped or gripped between shaft 246 and edge 274 of piece 242. The wrapped suture 22 does not lose tension because of the friction between it and one or both of shaft portion 246 and piece 242, particularly if suture 22 overlaps itself. Suture 22 remains between the narrowed part of shaft portion 246 and the surface of edge 274 of piece 242, and/or between part of piece 240 and a surface around or adjacent to slot 278. Piece 242 covers the part of suture 22 wrapped around or adjacent shaft 246, keeping other agents from contacting that portion of suture 22 and loosening it. In certain embodiments, the tolerances between pieces 240 and 242 are determined so that at least some of suture 22 is engaged by both pieces 240 and 242.

The portion of suture 22 extending from slot 278 can be cut off. In some embodiments suture 22 may be broken or cut by a surface of piece 242, e.g. one adjoining slot 278. A close fit of pieces 240 and 242 as indicated above provides pinching or friction on suture 22 to maintain its tension in addition to the friction or interference of any wrapping of suture 22 around piece 240.

With mechanism 226 assembled around suture 22 as indicated, the tension on suture 22 that holds the relevant portion of stomach S in position with respect to abdominal wall W is maintained. That tension holds tissue of stomach S and abdominal wall W together and presses mechanism 226 against the skin. Surface 250 in the illustrated embodiment of piece 240 spreads the tension force along a significant surface area of the skin, so as to minimize or eliminate discomfort, bruising, laceration by the suture, or other damage to the patient. With circular base portion 244 and rounded edge 252 of the illustrated embodiment, sharp edges do not dig into the skin. The configurations of pieces 240 and 242 maintain a relatively low profile next to the skin. Piece 242 is held so that it will not inadvertently loosen or disassemble from piece 240, yet a physician or other medical professional can pry piece 242 off with fingers or a prying tool inserted between pieces 240 and 242 (e.g. between edges 255 and 274).

Adjustment or release of tension on suture 22 can be accomplished substantially as indicated above. Piece 242 is removed from piece 240, suture 22 is unwrapped and/or adjusted as necessary, and piece 242 (or a new piece 242, if necessary) is re-snapped onto piece 240. Removal of piece 240 following unwinding of suture 22 results in suture 22 passing through lumen 262 and out of opening 266 in surface 250 of piece 240. The portion of suture 22 extending from the skin can be cut, and the anchor 24 and portion of suture 22 between anchor member 24 and the skin surface can pass into the gastrointestinal tract and be eliminated.

While pieces 240 and 242 of mechanism 226 are generally shown in the illustrated embodiment to be unconnected to each other prior to being snapped together, it will be understood that they may be connected in other embodiments to ensure that piece 242 is not lost prior to assembly. For example, a small connection C (e.g. a strip of plastic or other flexible material) may extend from a portion of piece 240 (e.g. the side of base 244) to the side or top of piece 242. The connection is placed so that it and piece 242 are not in the way or are easily moved out of the way during wrapping of suture 22 around piece 240, and so that it does not interfere with the snapping together of pieces 240, 242.

Suture 22 is of the type commonly used for existing suture anchors. Anchor member 24 may be made of a variety of materials and in a variety of configurations, as noted above. While metals can be used for anchor member 24, it is preferred to make anchor member 24 out of a biocompatible plastic or similar non-metallic item for MRI compatibility and to lessen the chance for piercing or other damage to tissue, particularly in the gastrointestinal tract.

Similarly, pieces 40 and 42 may be made of a variety of sturdy materials, but biocompatible, hypoallergenic plastic or similar non-metallic materials are preferred for similar reasons. The materials used for pieces 40, 42 are chosen to allow the squeezing or expansion of head 56 and/or the wall around hole 78 and to provide the stability necessary for the snapping engagement and hold noted above. In a particular embodiment, pieces 40 and 42 are injection molded using a polyurethane or other plastic soft enough for patient comfort yet hard enough to snap securely. High-friction materials or treatments (e.g. knurling) may be used for or placed on at least parts of pieces 40, 42 that are adjacent or in contact with suture 22. As noted above, the illustrated embodiments of pieces 40 and 42 are monolithic, while other embodiments are made of different parts screwed, welded or otherwise assembled together. The outer diameter of mechanism 26 is preferably about 0.5 inch (about 1.27 cm) or less and its thickness is preferably about 0.35 inch (about 0.90 cm) or less, so as to reduce bulk and lessen the chance of unintentionally contact with the mechanism.

Similar materials may be used to make pieces 240 and 242 of mechanism 226. As noted above, such parts may be made by injection molding using one or more substances. Plastics with durometers between 85A and 110D would be ideal for patient comfort. In a particular example, mechanism 226 may have a radius of about 5 mm and a height of about 3 mm. As indicated previously, mechanism 26 or 226 may be provided in some embodiments pre-threaded on suture 22 as a single product.

The example given above describing use of mechanism 26 in connection with a suture anchor 20 to move stomach tissue is merely one example. Mechanism 26 may be used in a variety of procedures in which suture anchors are used and in which tension on the suture anchor is to be maintained. Similarly, other types of procedures involving suture(s) under tension can use mechanism 26 in order to maintain the tension.

While embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It is to be noted that features particularly described above with respect to one or more embodiments may be used with or incorporated in other embodiments as well.

What is claimed is:

1. A method comprising:
    inserting a suture anchor having a suture into a patient so that the suture extends from the patient's body;
    wrapping a portion of the suture extending from a lumen in a shaft of a first piece of an external retention apparatus around the shaft of the first piece, the first piece having a bulbous head with a diameter larger than the shaft;
    following the wrapping, snapping a second piece onto the first piece so that at least part of the portion of the wrapped suture is between the first piece and the second piece, the second piece having an opening with a first lower portion with a first diameter approximately the same as the shaft and a second upper portion having a configuration flaring outward to accommodate the head of the first piece.

2. The method of claim 1, wherein the portion of the suture extends through the lumen of the first piece and out of the head, and is wrapped sufficiently so that the portion of the suture overlaps itself.

3. The method of claim 1, wherein the suture extends into the lumen of the first piece prior to insertion of the suture anchor into the patient.

4. The method of claim 1, wherein at least the first piece is threaded onto the suture after insertion of the suture anchor into the patient.

5. The method of claim 1, wherein the suture exits the first piece through the head and a portion exiting through the head is wrapped around the shaft.

6. The method of claim 1, wherein the suture exits the first piece through the shaft and is then wrapped around the shaft.

7. The method of claim 1, wherein the wrapping comprises wrapping the suture more than once around the shaft.

8. The method of claim 1, wherein the wrapping comprises wrapping the suture two to six times around the shaft.

9. The method of claim 1, wherein the shaft has a minimum-diameter portion proximal of a base portion that faces the patient's skin, and wherein the wrapping occurs in or adjacent to the minimum-diameter portion so that the suture is in or biased to move toward or into the minimum-diameter portion as it is wrapped.

10. The method of claim 1, wherein the suture does not double back on itself within the lumen.

11. The method of claim 1, wherein the suture extends through an inward-facing slot of the bulbous head of the first piece.

12. The method of claim 1, wherein the suture extends through a slot of the second piece.

13. The method of claim 1, wherein following the snapping step, the second piece is forced off of the first piece, the suture is unwrapped or otherwise adjusted with respect to the first piece.

14. The method of claim 13, further comprising snapping one of (a) the second piece back onto the first piece, and (b) a new second piece onto the first piece.

15. The method of claim 13, wherein the forcing the second piece off of the first piece comprises pulling the second piece off the first piece by hand.

16. The method of claim 13, wherein the forcing the second piece off of the first piece comprises inserting a prying element between the first and second piece.

17. The method of claim 1, wherein the first and second pieces are pre-connected by a connection that does not interfere with the snapping step.

18. A method for securing a suture extending from a patient, comprising:
    sliding the suture through a lumen of a first piece of an external suture retention apparatus, to provide a first suture portion residing in the lumen and a second suture portion external of a proximal opening of the lumen, the first piece including a shaft portion positioned above a base, the shaft portion having a smallest outer circumference that is less than a greatest outer circumference of a head portion of the first piece;
    wrapping the second suture portion around the shaft to provide a wrapped suture portion; and
    snapping a second piece having a snap fit opening including a first portion configured for close conforming fit around the shaft portion and a second portion configured to accommodate the head portion onto the first piece to trap the wrapped suture portion between the second piece and first piece.

19. The method of claim 18, wherein the first portion of the snap fit opening has a smallest outer circumference that is less than a greatest outer circumference of the second portion of the snap fit opening.

* * * * *